US011253641B2

(12) United States Patent
Zhang et al.

(10) Patent No.: US 11,253,641 B2
(45) Date of Patent: Feb. 22, 2022

(54) ANTI-REFLUX ENEMA BAG WITH PULLEY RESTRICTOR

(71) Applicant: Ningbo Albert Novosino Co., Ltd, Ningbo (CN)

(72) Inventors: Yonggui Zhang, Ningbo (CN); Haibo Hu, Ningbo (CN)

(73) Assignee: NINGBO ALBERT NOVOSINO CO., LTD., Ningbo (CN)

( * ) Notice: Subject to any disclaimer, the term of this patent is extended or adjusted under 35 U.S.C. 154(b) by 267 days.

(21) Appl. No.: 16/658,452

(22) Filed: Oct. 21, 2019

(65) Prior Publication Data

US 2020/0390963 A1 Dec. 17, 2020

(30) Foreign Application Priority Data

Jun. 13, 2019 (CN) .......................... 201920889455.1

(51) Int. Cl.
*A61M 3/02* (2006.01)
(52) U.S. Cl.
CPC ........ *A61M 3/0279* (2013.01); *A61M 3/0216* (2014.02); *A61M 3/0233* (2013.01)
(58) Field of Classification Search
None
See application file for complete search history.

(56) References Cited

U.S. PATENT DOCUMENTS

| 4,869,721 A  | * | 9/1989  | Karpisek ............. | A61M 39/286 604/250 |
| 2010/0217232 A1 | * | 8/2010  | Rosenblatt .......... | A61M 39/286 604/508 |
| 2010/0274214 A1 | * | 10/2010 | Frasier-Scott ........ | A61J 1/1462 604/408 |
| 2017/0281881 A1 | * | 10/2017 | Trevino .................. | A61M 1/82 |
| 2020/0215257 A1 | * | 7/2020  | Hagen ................. | A61M 3/0262 |

FOREIGN PATENT DOCUMENTS

CN            206454054       * 10/2016

* cited by examiner

*Primary Examiner* — Theodore J Stigell
*Assistant Examiner* — Rachel T. Smith
(74) *Attorney, Agent, or Firm* — Thomas | Horstemeyer, LLP

(57) ABSTRACT

Disclosed are various embodiments for an anti-reflux enema bag having a pulley restrictor that acts as a waterflow restrictor, where the enema bag is leakproof, easy-to-clean, and provides a steady flow of solution. An enema bag system includes an enema bag, a nozzle comprising a nozzle outlet, and an anti-reflux coupler positioned between the enema bag and the nozzle through which the solution passes from the enema bag to the nozzle outlet. The anti-reflux coupler comprises an inlet for receiving at least a portion of the solution from the enema bag; an outlet for expelling the solution into the nozzle; and a check valve configured to prevent reflux of the solution from the nozzle. The enema bag system further comprises a pulley restrictor configured to selectively control a speed at which the solution is introduced into the nozzle and expelled from the nozzle outlet.

19 Claims, 15 Drawing Sheets

ANTI-REFLUX ENEMA BAG WITH PULLEY RESTRICTOR

CROSS-REFERENCE TO RELATED APPLICATION

This application claims the benefit of and priority to Chinese Patent Application No. 201920889455.1 filed Jun. 13, 2019, the contents of which being incorporated by reference in their entirety herein.

TECHNICAL FIELD

This invention relates to the technical field of enema bags and, in particular, describes a washable anti-reflux enema bag system having a pulley restrictor and an anti-reflux coupler.

BACKGROUND

Enema bags include solution that can be utilized by patients and medical practitioners for cleansing the body, such as vaginal, anal, and other bodily cavities. Generally, enema bags are filled with a solution, such as clean water, which is injected into a cavity of a person through use of a syringe-type device coupled to the enema bag. During this process, the solution may "reflux," where some solution is returned into a tube positioned between an enema bag and a syringe device, thereby contaminating the solution and affecting the use of conventional enema bags. In some instances, the reflux can return to the enema bag and contaminate the solution residing therein.

Various types of enema bags can be suspended or hung to create natural water pressure that can be used in applying a desirable flow of solution. However, with existing enema bags, an opening for filling solution in the enema bag is intended to be small to prevent solution from spilling out during use, which makes filling the enema bag with solution difficult and inconvenient. Further, existing enema bags have switches or valves that do not completely stop solution from leaking when turned off, which also leads to a buildup of dirt or other debris. Even further, various components of the enema bag cannot be sterilized using, for example, boiling water, and cannot be disassembled for cleaning.

BRIEF SUMMARY OF INVENTION

Disclosed are various embodiments for an enema bag system that is leakproof, easy to disassemble and clean, prevents reflux, has components that can be independently cleaned and sanitized, and controls a rate at which water is expelled from a nozzle outlet. An enema bag system includes an enema bag, a nozzle comprising a nozzle outlet, and an anti-reflux coupler positioned between the enema bag and the nozzle through which the solution passes from the enema bag to the nozzle outlet. The anti-reflux coupler can include an inlet for receiving at least a portion of the solution from the enema bag, an outlet for expelling the solution into the nozzle, and a check valve configured to prevent reflux of the solution from the nozzle. The check valve can include one of an umbrella valve, a duckbill valve, a slit-cutting valve, and a flapper valve. The enema bag system can further include tubing fluidly coupling the enema bag, the anti-reflux coupler, and the nozzle.

The enema bag can include an enema bag opening at a top of the enema bag for filling the enema bag with solution. The enema bag system can further include an enema bag cover configured to rest on the top of the enema bag and cover the enema bag opening. In some embodiments, the enema bag system includes a hook positioned through an aperture in the nozzle bag and further positioned in a recess notched in the enema bag cover. The hook can include an S-shaped hook and a hanging of the enema bag system using the S-shaped hook or other hook can create water pressure that affects the speed at which the solution is expelled from the nozzle outlet.

In further embodiments, the enema bag system can include a pulley restrictor configured to selectively control a speed at which the solution is introduced into the nozzle and expelled from the nozzle outlet. The pulley restrictor can include a body, a guide, and a wheel movably coupled to the guide, the body comprising a first end and a second end. The tubing can be positioned through the body such that the wheel is positioned near (e.g., above or below) the tubing. An adjustment of the wheel along the guide to the first end of the body causes pressure to be applied to the tubing and restricts flow of the solution therein. Conversely, adjustment of the wheel along the guide to the second end of the body relieves the pressure on the tubing and permits the flow of the solution therein.

The body of the pulley restrictor can be triangular-shaped and comprise a recess through which the tubing is positioned. The guide can include a first track and a second track nested in opposing sides of the body of the pulley restrictor. As such, the wheel can include a first projection projecting from a first side of the wheel and a second projection projecting from a second side of the wheel, where the first projection is received in the first track and the second projection is received in the second track.

The enema bag system can further include a first connection at which the enema bag is removably coupled to the tubing, and a second connection at which the tubing is coupled to other tubing and the nozzle, where the second connection is provided by the anti-reflux coupler. At least one of the first connection and the second connection can be a threaded connection or an interference fit connection.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

DETAILED DESCRIPTION

Figure 1:
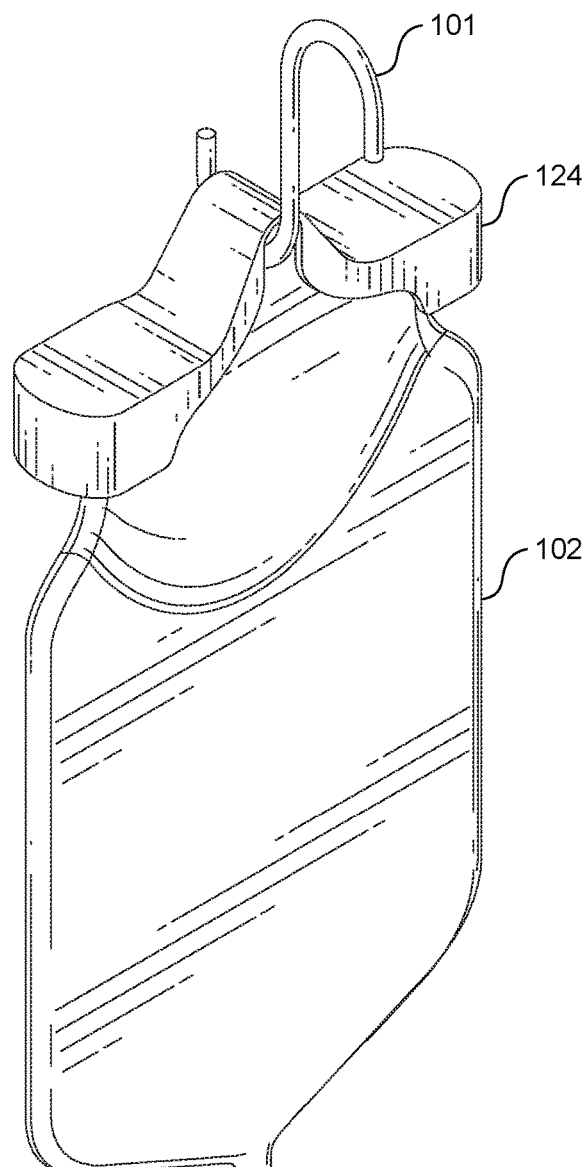
FIG. 1 is a perspective view of an enema bag system according to various embodiments of the present disclosure.
Figure 1:
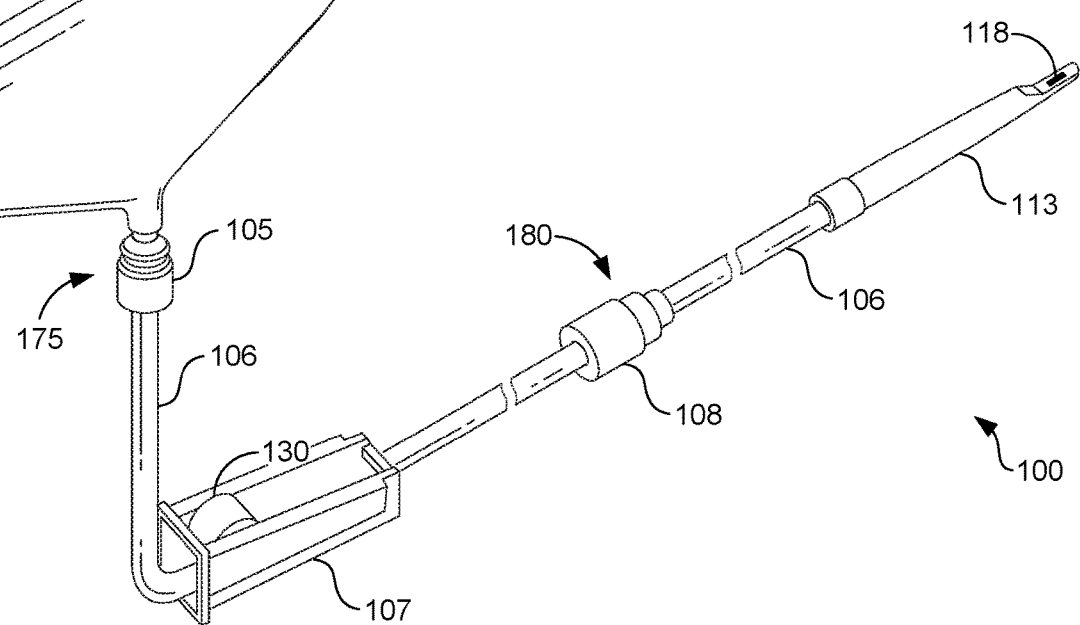

The present disclosure generally relates to an anti-reflux enema bag system having a pulley restrictor that is leak-proof, easy to disassemble and clean, prevents reflux, has components that can be independently cleaned and sanitized, and controls a rate at which water is expelled from a nozzle outlet. Some types of enema bags can be suspended at a certain height to create water pressure naturally that can be used in obtaining a desirable flow of solution. However, with existing enema bags, an opening for filling solution in the enema bag is designed to be small to prevent solution from spilling out during use, which makes filling the enema bag with solution difficult and inconvenient. Further, existing enema bags have valves that do not completely stop a flow of solution when turned off, which also leads to a buildup of dirt or other debris. Also, various components of the enema bag cannot be sterilized using, for example, boiling water, and cannot be disassembled for cleaning.

Accordingly, various embodiments are disclosed for an enema bag system that includes an enema bag, a nozzle comprising a nozzle outlet, and an anti-reflux coupler positioned between the enema bag and the nozzle through which the solution passes from the enema bag to the nozzle outlet. The anti-reflux coupler can include an inlet for receiving at least a portion of the solution from the enema bag, an outlet for expelling the solution into the nozzle, and a check valve configured to prevent reflux of the solution from the nozzle. The check valve can include one of an umbrella valve, a duckbill valve, a slit-cutting valve, and a flapper valve. The enema bag system can further include tubing fluidly coupling the enema bag, the anti-reflux coupler, and the nozzle.

The enema bag can include an enema bag opening at a top of the enema bag for filling the enema bag with solution. The enema bag system can further include an enema bag cover configured to rest on the top of the enema bag and cover the enema bag opening. In some embodiments, the enema bag system includes a hook positioned through an aperture in the nozzle bag and further positioned in a recess notched in the enema bag cover. The hook can include an S-shaped hook and a hanging of the enema bag system using the S-shaped hook or other hook can create water pressure that affects the speed at which the solution is expelled from the nozzle outlet.

In further embodiments, the enema bag system can include a pulley restrictor configured to selectively control a speed at which the solution is introduced into the nozzle and expelled from the nozzle outlet. The pulley restrictor can include a body, a guide, and a wheel movably coupled to the guide, the body comprising a first end and a second end. The tubing can be positioned through the body such that the wheel is positioned near (e.g., above or below) the tubing. An adjustment of the wheel along the guide to the first end of the body causes pressure to be applied to the tubing and restricts flow of the solution therein. Conversely, adjustment of the wheel along the guide to the second end of the body relieves the pressure on the tubing and permits the flow of the solution therein.

The body of the pulley restrictor can be triangular-shaped and comprise a recess through which the tubing is positioned. The guide can include a first track and a second track nested in opposing sides of the body of the pulley restrictor. As such, the wheel can include a first projection projecting from a first side of the wheel and a second projection projecting from a second side of the wheel, where the first projection is received in the first track and the second projection is received in the second track.

The enema bag system can further include a first connection at which the enema bag is removably coupled to the tubing, and a second connection at which the tubing is coupled to other tubing and the nozzle, the second connection being provided by the anti-reflux coupler. At least one of the first connection and the second connection is a threaded connection or an interference fit connection.

Figure 2:
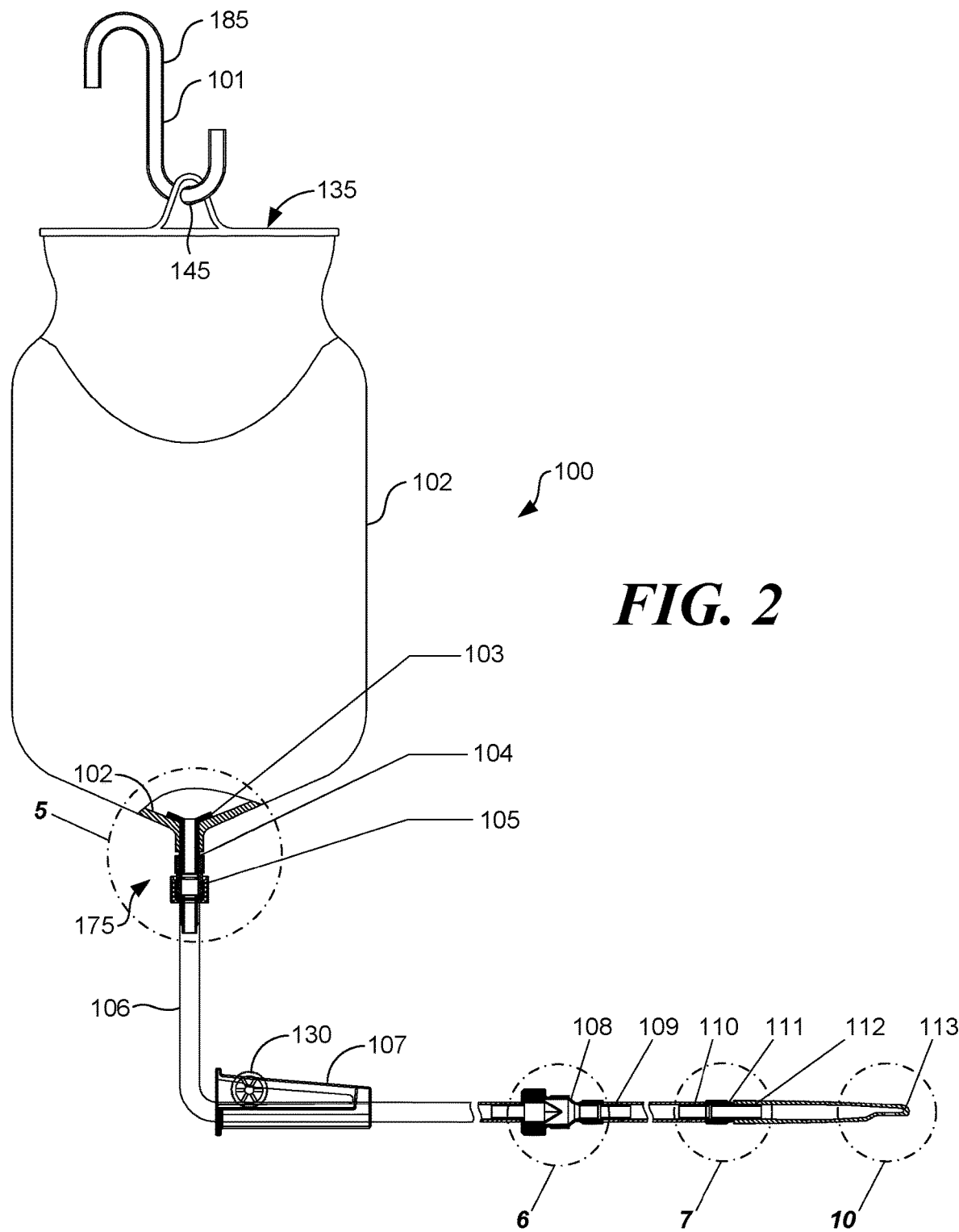
FIGS. 2 and 3 are side elevation views of the enema bag system according to various embodiments of the present disclosure.
Figure 3:
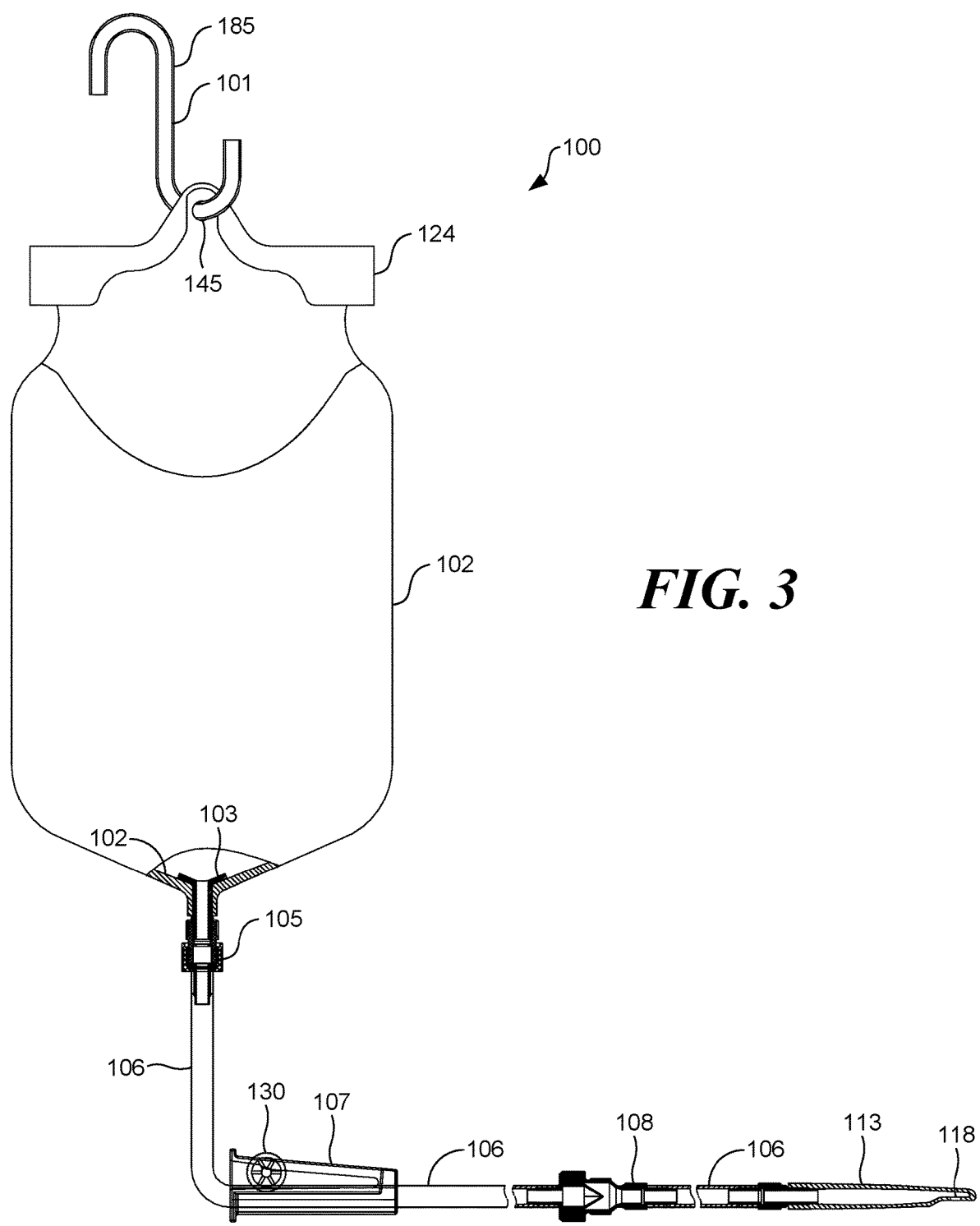

Turning now to FIGS. 1-3, various views of an enema bag system 100 is shown according to various embodiments. FIG. 1 is a perspective view of the enema bag system 100 according to various embodiments. FIGS. 2 and 3 are side elevation views of the enema bag system 100 according to various embodiments.

The enema bag system 100 can include, for example, a hook 101, an enema bag 102 having an enema bag body, a Y-shaped connector 103, a first O-ring 104, a three-piece sleeve 105, tubing 106, a pulley restrictor 107, anti-reflux coupler 108 having a one-way valve, such as a duckbill valve 115, a first M10 female connector 109, a second M10 female connector 110, a second O-ring 111, a first M10 male connector 112, an enema nozzle 113, an anti-reflux male connector 114, an anti-reflux female connector 116, a bevel 117, a nozzle outlet 118, internal and outer thread connectors 119, movable nut 120, inner tube connector 122, outer diameter sharp corner 123, enema bag cover 124, first convex 125, second convex 126, third convex 127, as well as other components as will be discussed.

Referring collectively to FIGS. 1-16, the enema bag system 100 can include an enema bag 102, an enema nozzle 113 comprising a nozzle outlet 118, and an anti-reflux coupler 108 positioned between the enema bag 102 and the enema nozzle 113 through which solution passes from the enema bag 102 to the nozzle outlet 118. The anti-reflux coupler 108 can include an inlet for receiving at least a portion of the solution from the enema bag 102, an outlet for expelling the solution into the enema nozzle 113, and a one-way check valve configured to prevent reflux of the solution from the enema nozzle 113, as will be discussed. For instance, the check valve can include one of an umbrella valve, a duckbill valve 115, a slit-cutting valve, and a flapper valve in some embodiments. The enema bag system 100 can further include tubing 106 fluidly coupling the enema bag 102, the anti-reflux coupler 108, the enema nozzle 113, as well as other components shown or described.

The enema bag 102 can include an enema bag opening 135 at a top of the enema bag 102 that can be used for filling the enema bag with solution, such as clean water, soapy water, tea, coffee, or other solution used for enemas. In some embodiments, the enema bag opening 135 can be referred to as a "wide-mouth" opening, as the enema bag opening 135 has a width substantially similar to a top of the enema bag 102. The enema bag system 100 can further include an enema bag cover 124 configured to rest on the top of the enema bag 102 and cover all or a substantial portion of the enema bag opening 135. As such, the enema bag cover 124 can prevent dirt, insects, and other debris from being introduced into the solution and/or the enema bag system 100 during use or while in storage. In some embodiments, the enema bag cover 124 forms an interference fit with the top of the enema bag 102. Alternatively, the enema bag cover 124 may be coupled to the enema bag 102 using a connector or other means.

In some embodiments, the enema bag system 100 can include a hook 101 positioned through an aperture in the enema bag 102. Further, the hook 101 can be positioned in a through-hole 145 notched in or defined by the enema bag cover 124 as well as a recess 140 in the enema bag cover 124. The hook 101 can include an S-shaped hook convenient for hanging in some embodiments, or other appropriate shaped hook as can be appreciated. The hanging of the enema bag system 100 using the hook 101, such as an S-shaped hook or other hook, can create water pressure that affects the speed at which the solution is expelled from the enema nozzle 113 and the nozzle outlet 118.

Figure 4A:
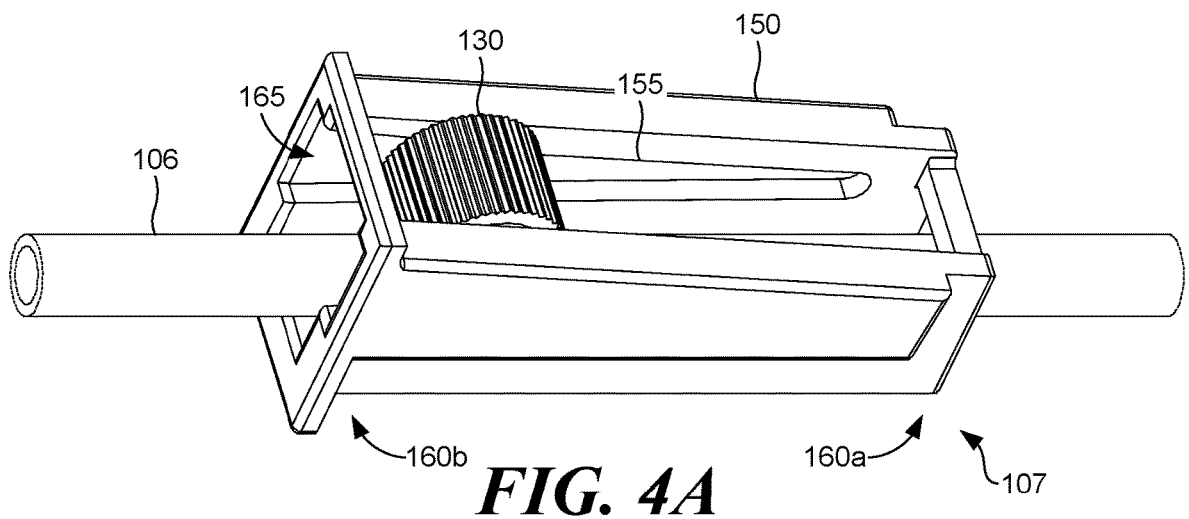
FIGS. 4A and 4B are perspective views of a pulley restrictor of the enema bag system according to various embodiments of the present disclosure.
Figure 4B:
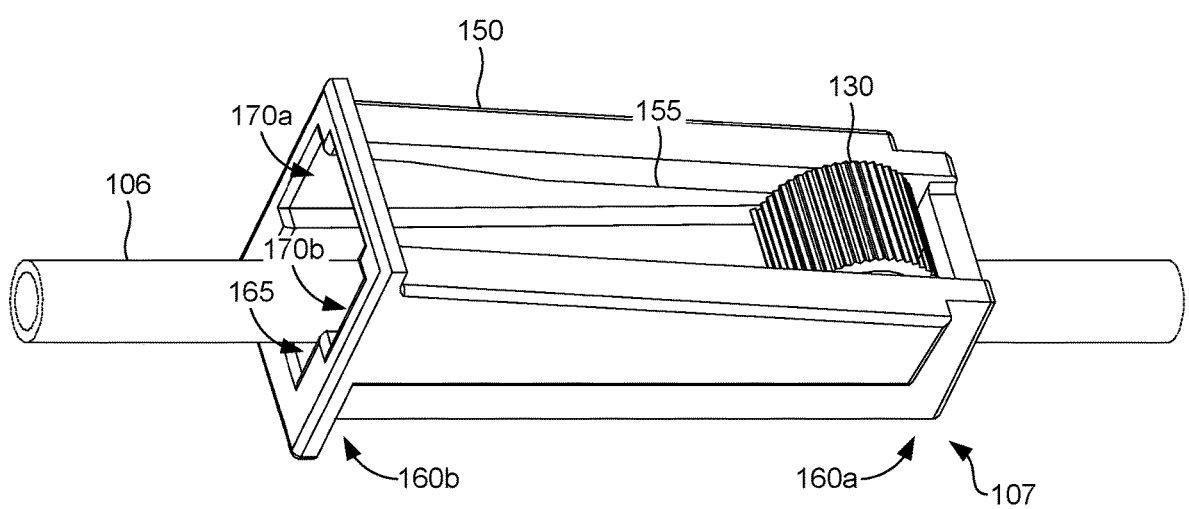
Figure 5:
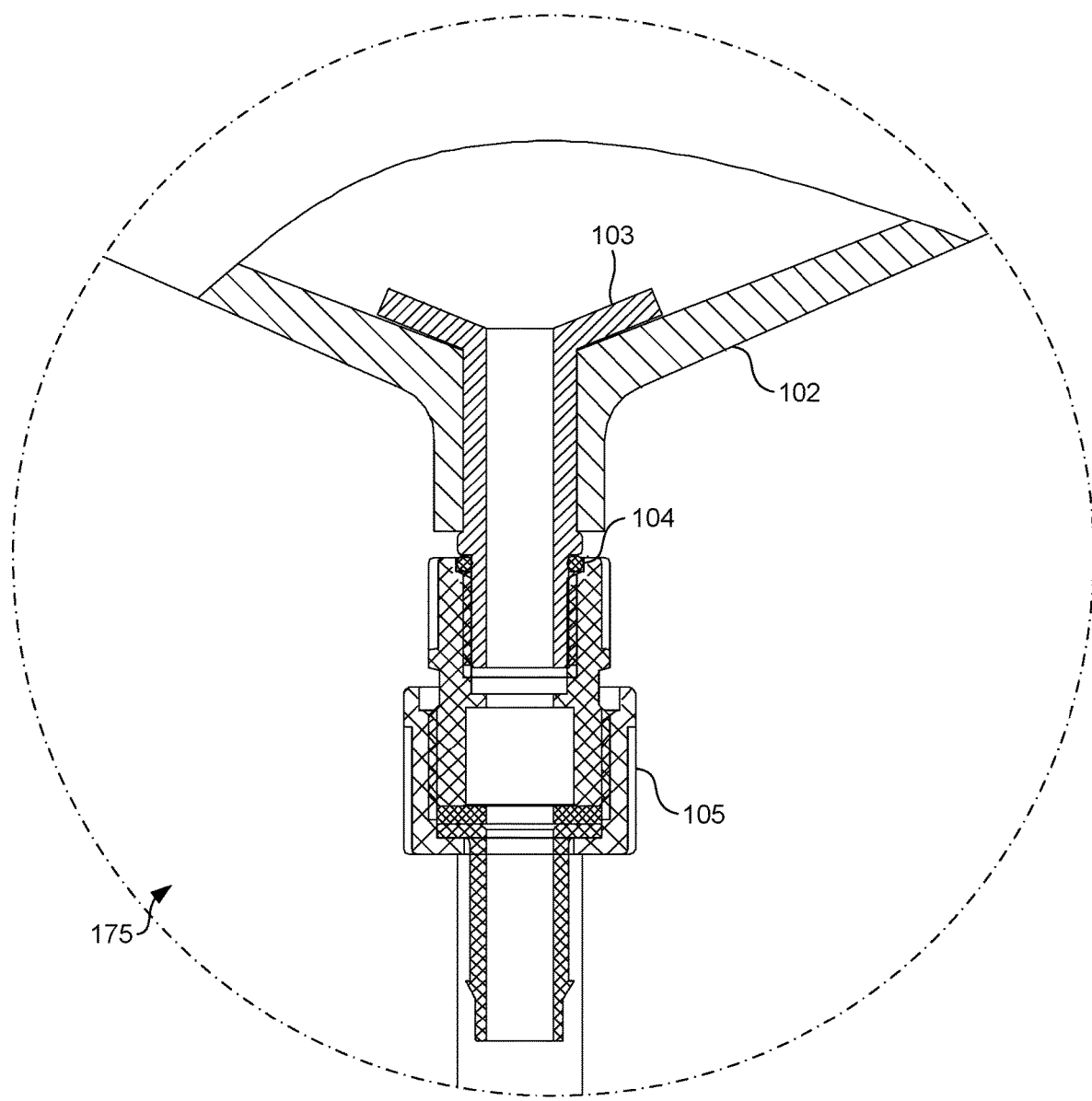
FIG. 5 is a partial enlarged view of callout region 5 of FIG. 2 according to various embodiments of the present disclosure.

Turning now to FIGS. 4A and 4B, views of the pulley restrictor 107 of the enema bag system 100 are shown according to various embodiments of the present disclosure. In various embodiments, the enema bag system 100 can include a pulley restrictor 107 configured to selectively control a speed at which the solution is introduced into the enema nozzle 113 and expelled from the nozzle outlet 118. The pulley restrictor 107 can include a body 150 (or "pulley restrictor body"), a guide 155, and a wheel 130 movably coupled to the guide 155, where the body 150 has a first end 160a and a second end 160b. The tubing 106 can be positioned through an aperture 165 of the body such that the wheel 130 is positioned above, below, to the side of, or otherwise near the tubing 106. The guide 155 is angled downwards in some examples which causes a relative vertical position of the wheel 130 to adjust, for instance, through rotation of the wheel 130 using a thumb or finger of the operator which can cause the wheel 130 to come into contact with the tubing 106.

As shown between the views of FIGS. 4A and 4B, an adjustment of the wheel 130 along the guide 155 to the first end 160 of the body 150 (e.g., rotating the wheel 130 in a first or second horizontal direction) causes a vertical position of the wheel 130 relative to the tubing 106 to move downwards, causing the wheel 130 to apply pressure to a surface of the tubing 106, thereby restricting flow of any solution therein. Conversely, adjustment of the wheel 130 along the guide 155 to the second end 160b of the body 150 relieves the pressure on the tubing 106 and permits the flow of the solution therein. In other words, when the wheel 130 is moved to the second end 160b of the body 150, the wheel 130 has no or negligible contact with the tubing 106.

The body 150 of the pulley restrictor 107 can be triangular-shaped. Further, the body 150 of the pulley restrictor 107 may comprise an aperture 165 through which the tubing 106 is positioned. The guide 155 can include a first track 170a and a second track 170b nested in opposing sides of the body 150 of the pulley restrictor 107. As such, the wheel 130 can include a first projection (not shown) projecting from a first side of the wheel 130 and a second projection projecting from a second side of the wheel 130, where the first projection is received in the first track 170a and the second projection is received in the second track 170b, as may be appreciated.

Referring again to FIGS. 1-3, the enema bag system 100 can further include a first connection 175 at which the enema bag 102 is removably coupled to the tubing 106, and a second connection 180 at which the tubing is coupled to other tubing and the enema nozzle 113. In some embodiments, the second connection 180 is provided via the anti-reflux coupler 108. At least one of the first connection 175 and the second connection 180 is a threaded connection or an interference fit connection.

The enema bag opening 135 can include a wide caliber or wide-mouth design, which is convenient for filling solution into the enema bag 102 as well as cleaning the enema bag 102. The first connection 175 can include a Y-shaped connector 103 provided under the enema bag 102 with a connector, such as a threaded connector, for coupling to the tubing 106. The connection is firm, while providing a good seal to prevent leakage from occurring at the first connection 175.

As noted above, the tubing 106 is provided with a pulley restrictor 107, which is convenient for an operator to easily adjust toggle the solution (e.g., on or off) as well as the speed of the solution with a single hand, enhancing comfort when using the enema bag system 100. The anti-reflux coupler 108 has a good flow rate, and the valve has a good anti-reflux effect. In some embodiments, the anti-reflux coupler 108 can be referred to as washable anti-reflux duckbilled one-way valve. As such, reflux of solution is avoided, and the anti-reflux coupler 108 can be separately disassembled and disinfected.

In some embodiments, the enema nozzle 113 has a flat design with no burr, and is smooth, comfortable, and can expel solution from the sides and/or the tip. The enema bag 102, the pulley restrictor 107, the anti-reflux coupler 108, and tubing 106 can be boiled, disinfected, sterilized, or otherwise cleaned by disassembling the respective components.

As shown in FIGS. 1 to 16, the enema bag 102 with pulley restrictor 107 can be removed and washed, and the hook 101 can be arranged on a hook hole (not shown) of the enema bag 102 and/or a through-hole 145 defined in or by a shape of the enema bag cover 124.

There is an enema bag body of the enema bag 102. In some embodiments, the enema bag 102 is formed of silicone or other suitable materials for convenient cleaning and durability. The lower part of the body of the enema bag 102 can be provided with a Y-shaped connector 103. The lower part of the Y-shaped connector 103 can be provided with a three-piece sleeve 105, also referred to as a bag-and-tube coupler. The Y-shaped connector 103 and the three-piece sleeve 105 are provided with a first O-ring 104, where the first O-ring 104 and the three-piece sleeve 105 form a seal. The three-piece sleeve 105 can be tightly fitted with the tubing 106, which can be formed of silicone in some embodiments. The tubing 106 may be connected with the pulley restrictor 107 that can be used to adjust the speed or stop the flow of the solution.

The portion of the tubing 106 positioned below the pulley restrictor 107 is provided with the anti-reflux coupler 108, which can be removable and fixed on the tubing 106 by way of a straight insertion (e.g., interference fit) although in some embodiments a threaded connection can be employed. The anti-reflux coupler 108 may be externally connected with a first M10 female connector 109, where the first M10 female connector 109 is provided with an O-ring. The O-ring may form a sealed connection with the first M10 female connector 109. The other end of the tubing 106 may be tightly sealed with a second M10 female connector 110, where the first M10 female connector 109 is disposed under the second M10 female connector 110. Further, a first M10 male connector 112 may be sleeved with a second O-ring 111, and the first M10 male connector 112 may be connected with a straight enema mouth of the enema nozzle 113, and the distal end of the enema nozzle 113 is provided with a nozzle outlet 118.

Figure 6:
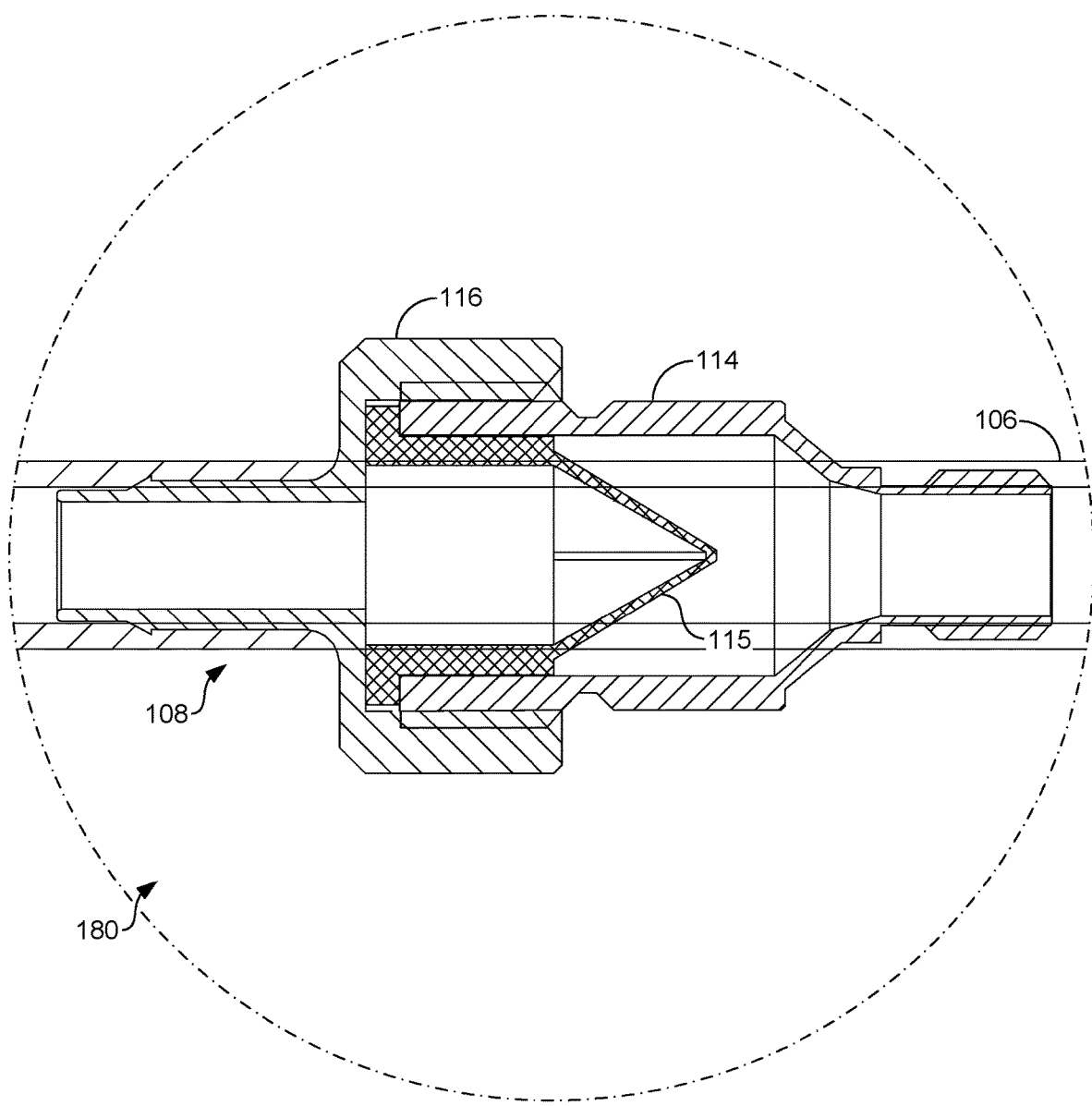
FIG. 6 is a partial enlarged view of callout region 6 of FIG. 2 according to various embodiments of the present disclosure.
Figure 7:
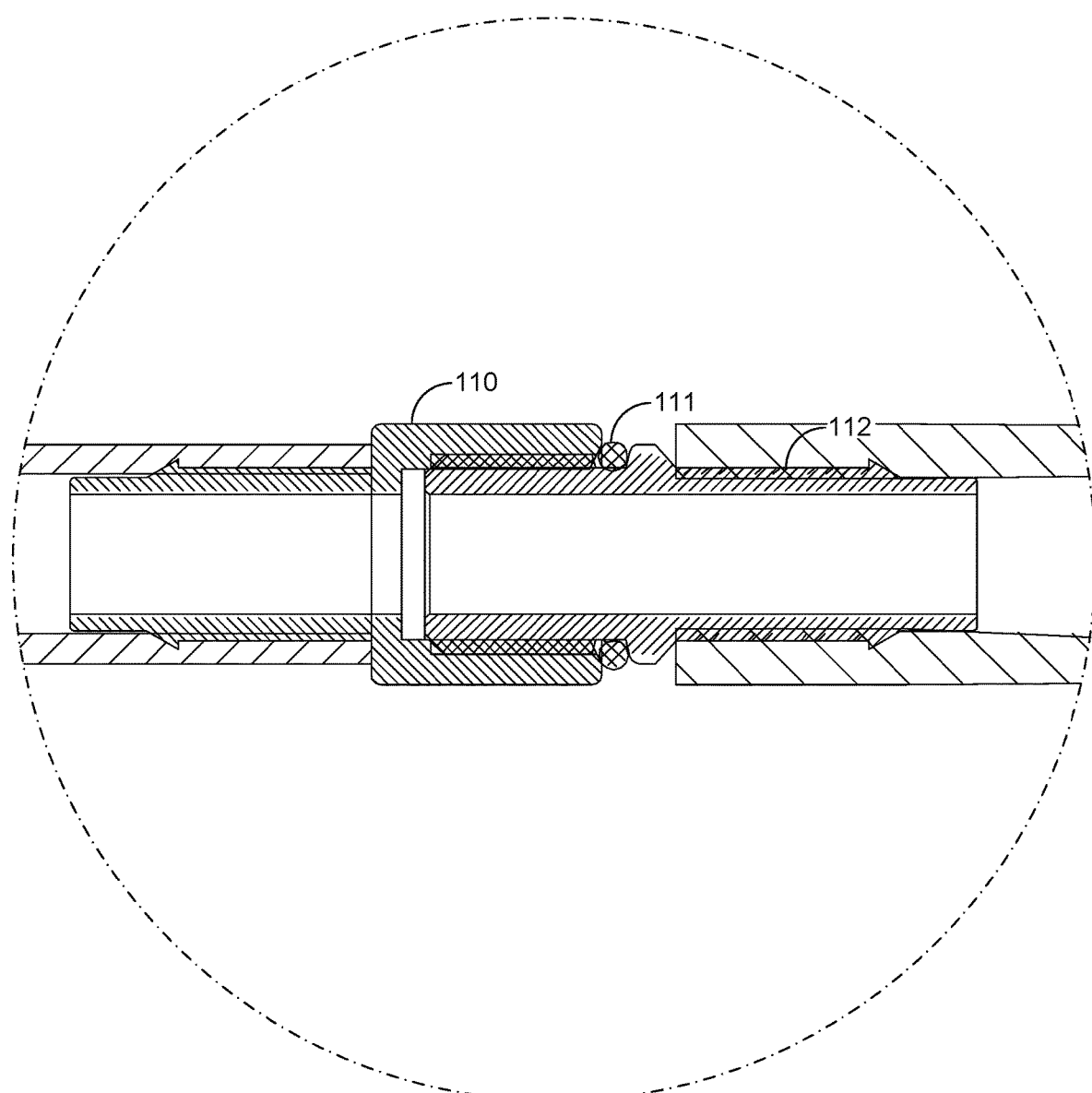
FIG. 7 is a partial enlarged view of callout region 7 of FIG. 2 according to various embodiments of the present disclosure.
Figure 8A:
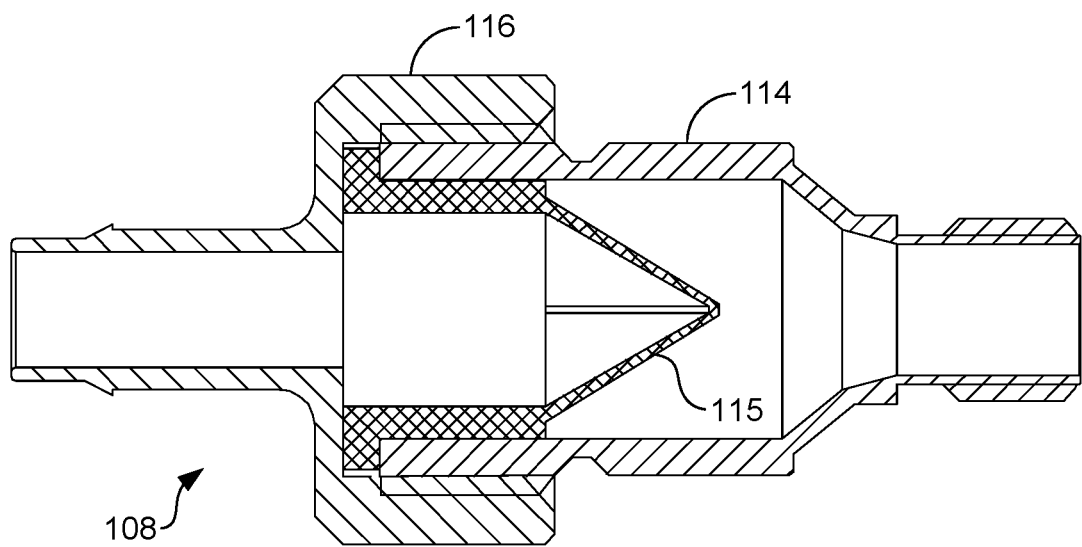
FIGS. 8A and 8B are side cross-section view of an anti-reflux coupler according to various embodiments of the present disclosure.
Figure 8B:
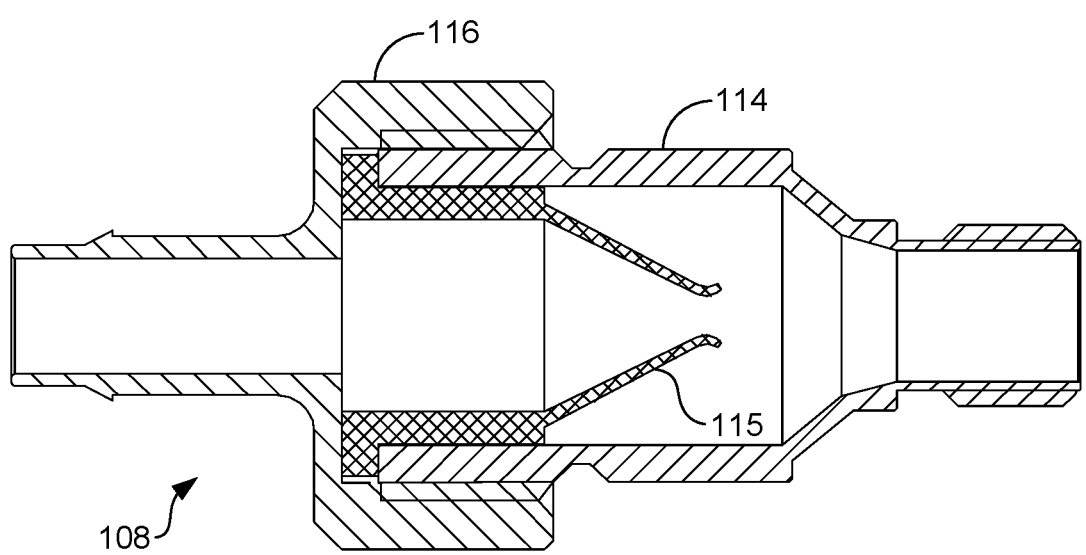

As shown in FIG. 6, the anti-reflux coupler 108 comprises various components, such as the anti-reflux male connector 114, the duckbill valve 115, the anti-reflux female connector 116. The anti-reflux female connector 116 and the anti-reflux male connector 114 may use a threaded connection in some embodiments. The duckbill valve 115 may be disposed in the anti-reflux male connector 114. The fitting may include a threaded structure that is detachable while providing a good sealing effect. Further, the anti-reflux coupler 108 is washable, can be sterilized repeatedly at high temperature, and is durable. In some embodiments, the duckbill valve 115 may be made of a silicone material. FIGS. 8A and 8B are side cross-section views of the anti-reflux coupler 108 according to various embodiments of the present disclosure, where the duckbill valve 115 is shown in a closed and an open position, respectively.

In some embodiments, the enema bag system 100 is provided with one or more S-shaped stainless-steel hooks, and the S-hook material is made of 304 stainless steel material, which is firm and solid and provided the S-hook with a smooth and burn-free surface. At the same time, a jacket 185, such as an S-hook jacket, may be positioned over the hook 101. To this end, the jacket 185 may include a size and shape substantially similar to the hook 101, and include a transparent Polyvinyl chloride (PVC) tube that provides an anti-skid effect. The hook 101 (e.g., S-shaped hook) can be easily inserted into the through-hole 145 of the enema bag 102 so that the enema bag 102, and components coupled thereto, can be firmly hung. Notably, the special shape design of the S-shaped hook makes it easy for an operator to hang the enema bag system 100 on hooks behind a door, in the bathroom and the bedroom, while providing a steady connection. The through-hole 145 can include a two double-ear hole design (e.g., a first hole on a first side of the enema bag 102 and a second hole on a second side of the enema bag 102 with the enema bag opening 135 positioned therebetween), which avoids spilling of any solution.

The enema bag cover 124 may be positioned above the body of the enema bag 102. In some embodiments, the enema bag cover 124 is made of Polypropylene (PP), such as medical grade PP. As such, the enema bag cover 124 can be break-resistant and repeatedly boiled for sterilization. The special inner wide opening design completely covers the periphery of the body of the enema bag 102, and is clamped in the middle of the hook 101. It is not easy to fall, but can cover the enema bag opening 135. When the enema bag system 100 is in use, the enema bag cover 124 can prevent dirt, insects, and other debris from falling into the enema bag 102. However, when solution is to be added, the enema bag cover 124 can be easily removed.

In various embodiments, the body of the enema bag 102 is made of medical grade silicone material, which is not easily broken or damaged. As such, the enema bag 102 can be repeatedly boiled and disinfected while maintaining durability. At the same time, the body of the enema bag 102 has a wide-mouth opening, which is convenient for filing the enema bag 102 with solution, and is also convenient for the operator to thoroughly clean and disinfect before or after use. The enema bag 102 can be used not only for water-based enemas, but also for coffee-based enemas and tea-based enemas.

The silicone bag body has a Y-shaped connector 103. The Y-shaped connector 103 comprises a sleeve that is tightly sealed and tightly connected inside the body of the enema bag 102. If the operator moves the enema bag 102 during use, the enema bag 102 and the tubing 106 do not easily separate and do not leak water or other solution. In some embodiments, the Y-shaped connector 103 is externally threaded, and the external thread is covered with an O-ring, such as a silicone O-ring, which forms a tight seal with the internal thread of the three-piece sleeve 105. As such, water leakage does not easily occur, and it is convenient for the operator to assemble and disassemble the tubing 106 for cleaning, disinfection, or storage.

The three-piece sleeve 105 in the tubing 106 can be formed of medical grade PP plastic. The three-piece sleeve 105 can be disassembled and cleaned, and can be boiled at a high temperature. The three-piece sleeve 105 can include a silicone sealing gasket having a strong sealing effect, while not easily causing leakage. The three-piece sleeve 105 can include the internal thread and the external thread of the Y-shaped connector 103 with an O-ring, thereby offering a threaded tight seal connection that does not leak solution. The other end of the three-piece sleeve 105 can include a straight releasing design (e.g., a friction fit) that is tightly sealed with silicone or other suitable material that offers a firm connection, thus avoiding the components from easily disassembling from one another. The three-piece sleeve 105 comprises an inner cap that is mobile, the tubing 106 will not be twisted and entangled when disassembling and assembling the tubing 106, which is convenient for the operator to easily disassemble and clean the tubing 106.

The pulley restrictor 107 can be formed of medical grade PP plastic. As such, the pulley restrictor 107 can be boiled at high temperature before or after use. The pulley restrictor 107 can include a smooth and burr-free surface. The pulley restrictor 107 has a unique shape and a special tooth-shaped or triangular-shaped body. The sliding pulley position of the wheel 130 can be used to clamp the tubing 106, for instance, to adjust the flow rate of the solution flowing therein. The pulley restrictor 107 does not create two other coupling points along the tubing 106 where leakage can occur. The assembly and disassembly of the pulley restrictor 107 is convenient for cleaning and disinfection. The pulley restrictor 107 also has a wide shape, which is convenient for the operator to easily grasp with one hand and rotate the wheel 130 using a single finger (e.g., the thumb of the operator). The position of the wheel 130 in the pulley restrictor 107 enables the enema speed to increase the comfort of an enema by controlling the rate of flow of the solution. When the operator wishes to stop the enema, the position of the wheel 130 in the pulley restrictor 107 can be easily adjusted to stop the flow.

The anti-reflux coupler 108 can be composed of three or more components, such as an anti-reflux male connector 114, the duckbill valve 115 (which may be formed of silicone), and an anti-reflux female connector 116. The three fittings may be connected using a threaded connection that provides a good seal. The threaded connection can make it convenient for the operator to open and repeat high-temperature disinfection of the components. Also, the anti-reflux coupler 108 is durable, detachable, and provides a notable anti-reverse effect, which causes sewage to not return to the tubing 106 on other component connected thereto. At the same time, the water output of the duckbill valve 115, or other suitable valve, does not cause leakage of water, thereby saving solution.

Figure 9:
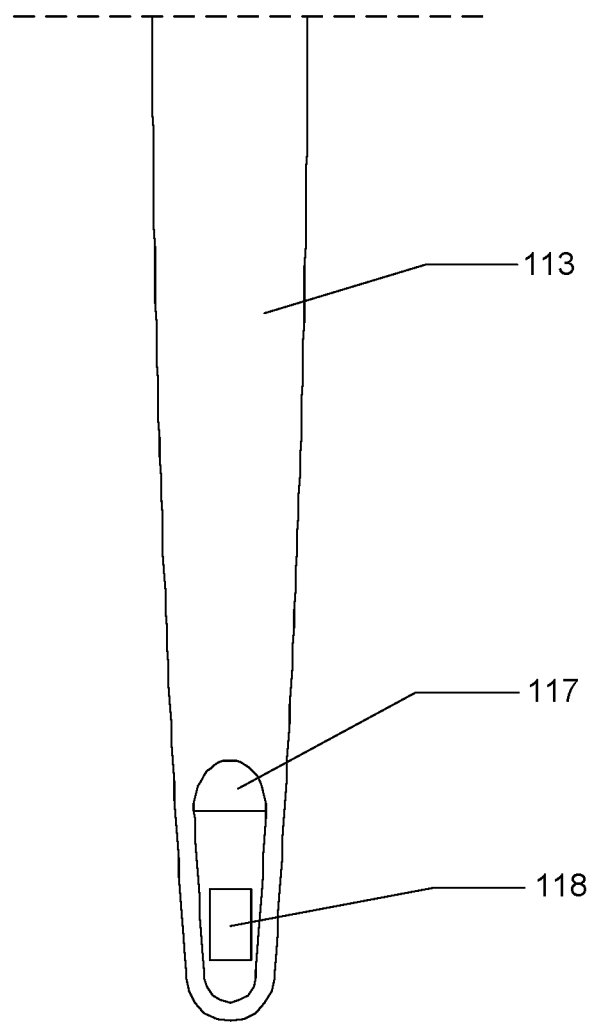
FIG. 9 is a bottom view of a nozzle of the enema bag system according to various embodiments of the present disclosure.
Figure 10:
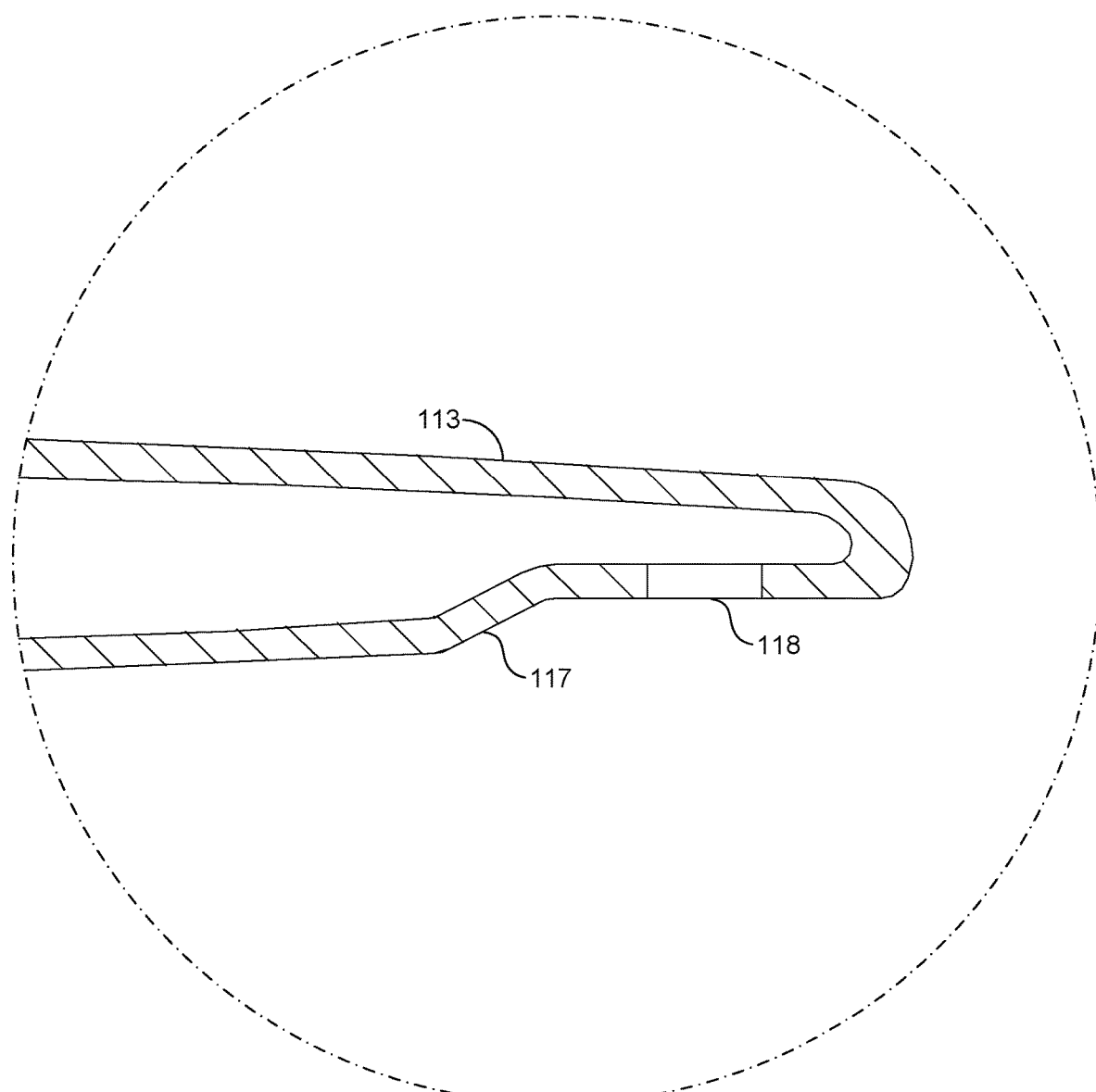
FIG. 10 is a side cross-section view of the nozzle of the enema bag system according to various embodiments of the present disclosure.

As shown in FIG. 9, the enema nozzle 113 can include a straight-faced enema tip that is environmentally-friendly and durable for medical soft materials. The enema nozzle 113 includes smooth and burr-free surfaces and, in some embodiments, a head of the enema nozzle 113 is partially straight, as depicted in FIGS. 1 and 9. The nozzle outlet 118 can include a large-flow outlet positioned on a side of a bevel 117 offset from a general surface of the enema nozzle 113. A straight face enema tip is thereby provided. Due to the straight-head design and the single-sided flat design, the nozzle outlet 118 can be provided on the flat side, such that the nozzle outlet 118 is less likely to block after entering the human body than an ordinary outer surface hole. The bevel 117 can be positioned below the nozzle outlet 118 as a transitioning tip design, ensuring that the solution entering the human body enters more smoothly. The surface of the washing head has no clamping lines and is without corners or sharp changes in surfaces, and the nozzle outlet 118 is arranged on the plane, where the injection mold is a plane impact mold, avoiding burrs and flashing on the surface of the enema nozzle 113. As such, the enema nozzle 113 will not scratch the operator or cause any tingling sensation when entering the body while blocking the nozzle outlet 118.

As may be appreciated based on the foregoing disclosure, the anti-reflux enema bag system 100 having a pulley restrictor 107 includes an enema bag 102, three-piece sleeve 105, tubing 106, an anti-reflux coupler 108, O-rings, the first M10 male connector 112, the first M10 female connector 109, the second M10 female connector 110, and other components can be assembled or disassembled such that the components can be disinfected by boiling water.

In this case, the enema bag 102 can be removed from the tubing 106 in a silicone tube assembly with the three-piece sleeve 105 before use. Then, the remaining tubing 106 and the enema bag 102 can be boiled in boiling water for five to ten minutes. After being disinfected with boiling water, the tubing 106 and the enema bag 102 are removed and dried out. Then, the three-piece sleeve 105 can be connected to the Y-shaped connector 103 of the enema bag 102. Thereafter, the enema nozzle 113 can be coupled to the second M10 female connector 110 on the silicone tube assembly. The wheel 130 of the pulley restrictor 107 can be returned to a closed state. The hook 101 can be inserted into a first one of the through-holes 145 in the enema bag 102. Warm enema solution can be poured or pumped into the enema bag 102 via the enema bag opening 135.

After the solution has been stored in the enema bag 102, a second one of the through-holes 145 can be placed onto the hook 101, and the enema bag system 100 with the solution is suspended to a certain height. The operator may then use the pulley restrictor 107 to slowly adjust the tubing 106 to an open state, and the flow rate is as small as possible until after the air of the tube assembly is exhausted. The solution has a certain pressure in a state of natural suspension, and the solution of the duckbill valve 115 in the anti-reflux coupler 108 is discharged through the tubing 106 to the enema nozzle 113 to discharge the solution. Then, the wheel 130 of the pulley restrictor 107 is adjusted to a "closed" state where the wheel 130 applies pressure to the tubing 106.

The enema nozzle 113 can be coated with an organic lubricant, the posture of the operator is adjusted, and the enema nozzle 113 is inserted into a cavity of the operator to be cleansed. The pulley restrictor 107 is adjusted to an "on" state by adjustment of the wheel 130 to start the enema. During the enema process, due to a certain pressure in the human body, sewage will be returned to the tubing 106. At this time, the duckbill valve 115, or other valve type, in the anti-reflux coupler 108 will be subjected to a reaction force, and the duckbill valve 115 is completely closed, as shown in FIG. 8A. In this case, sewage will not be recirculated. Accordingly, an anti-reflux enema bag system 100 is provided with a pulley restrictor 107 having a strong sealing effect without leaks. As such, solution can be applied with little or no loss.

Figure 11:
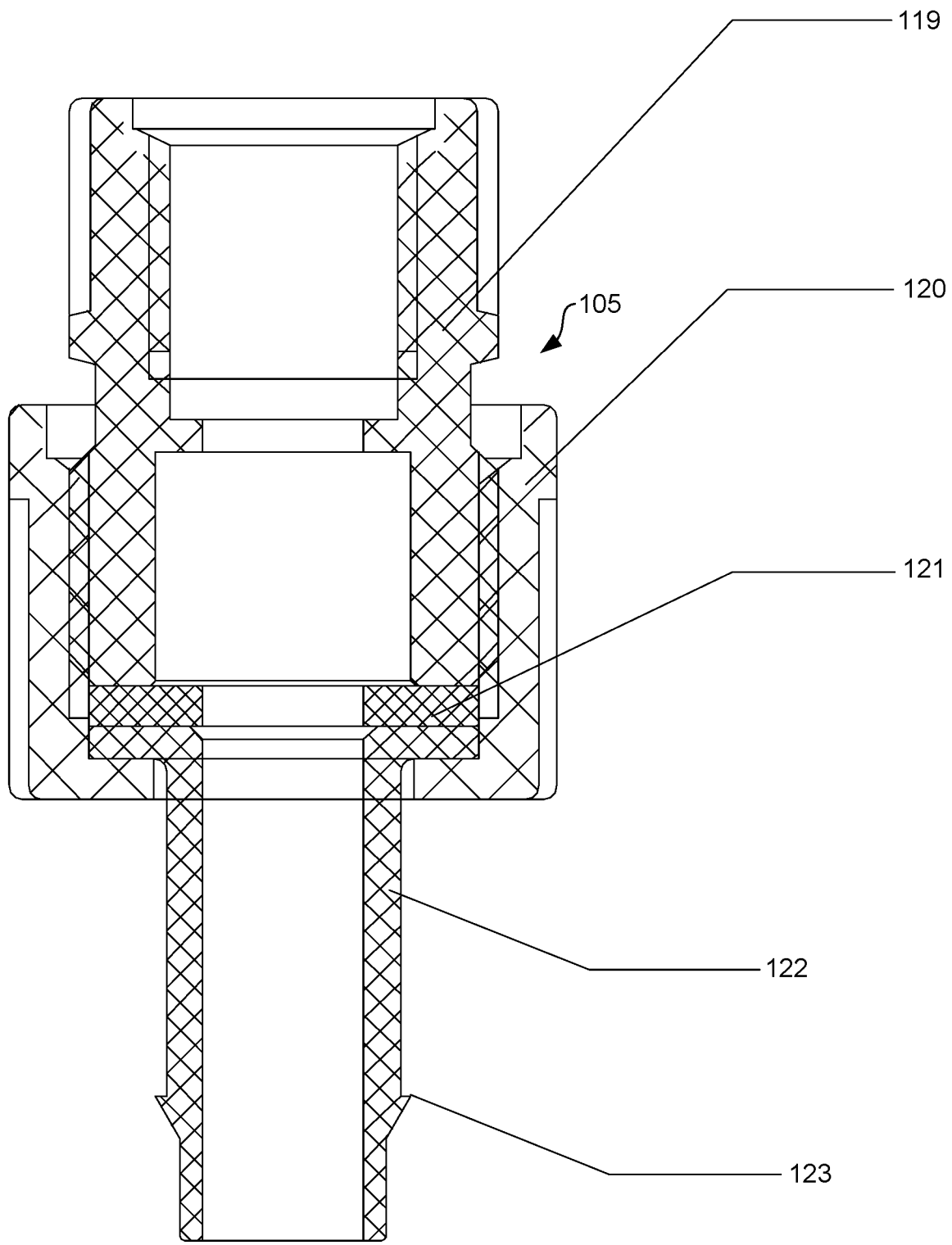
FIG. 11 is an enlarged cross-section view of a three-piece sleeve according to various embodiments of the present disclosure.

Referring next to FIG. 11, an enlarged cross-section view of the three-piece sleeve 105 is shown according to various embodiments of the present disclosure. To interact with the three-piece sleeve 105, one hand of the operator can pinch anti-skip ribs of inner and outer thread connectors 119, and the other hand can loosen a movable nut 120 counterclockwise to let the movable nut fall off the outer thread of the inner and outer thread connector 119, thereby causing the movable nut 120 and the inner tube connector 122 to separate. It is important to note that, when the movable nut 120 rotates, the inner tube connector 122 does not rotate, such that the tubing 106 does not rotate nor wrap. A sealing gasket 121 in the three-piece sleeve 105 can be made of a silicone material that provides strong sealing.

Figure 12:
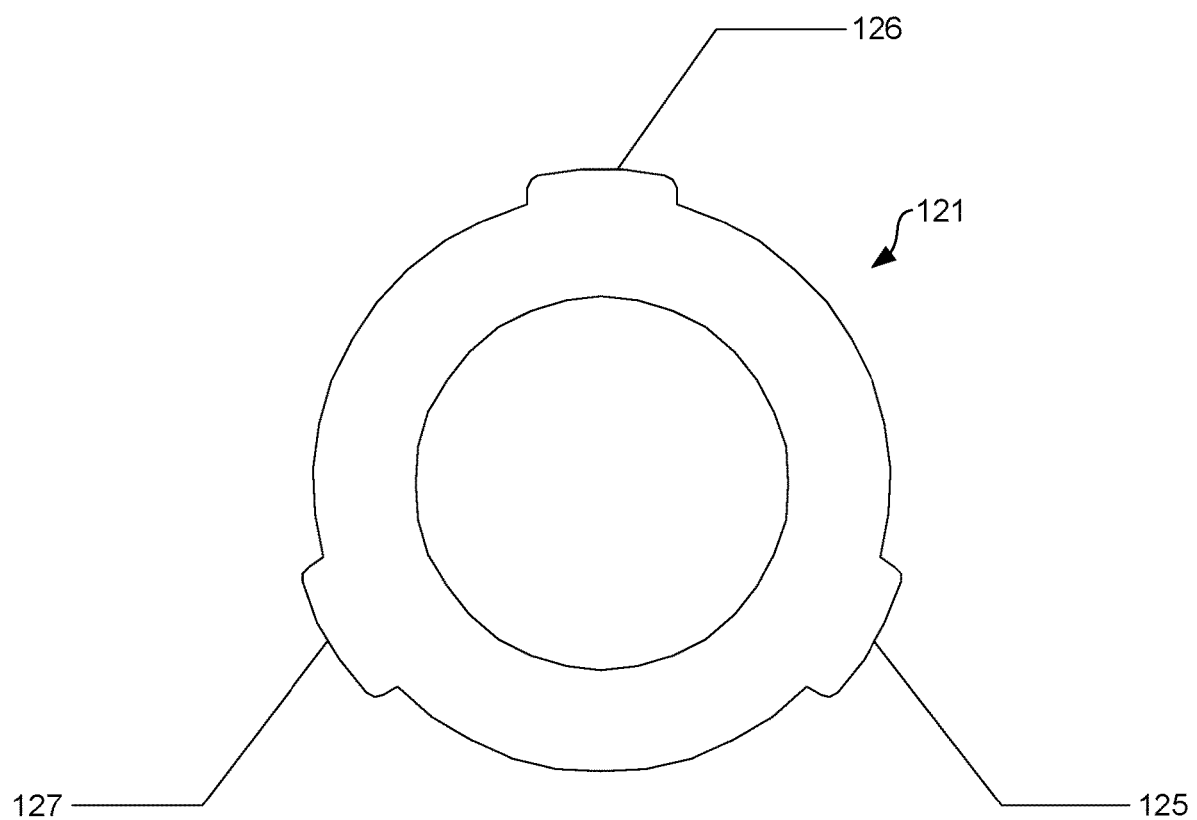
FIG. 12 is an enlarged top view of a sealing ring for use in the bag-and-tube coupler according to various embodiments of the present disclosure.
Figure 13:
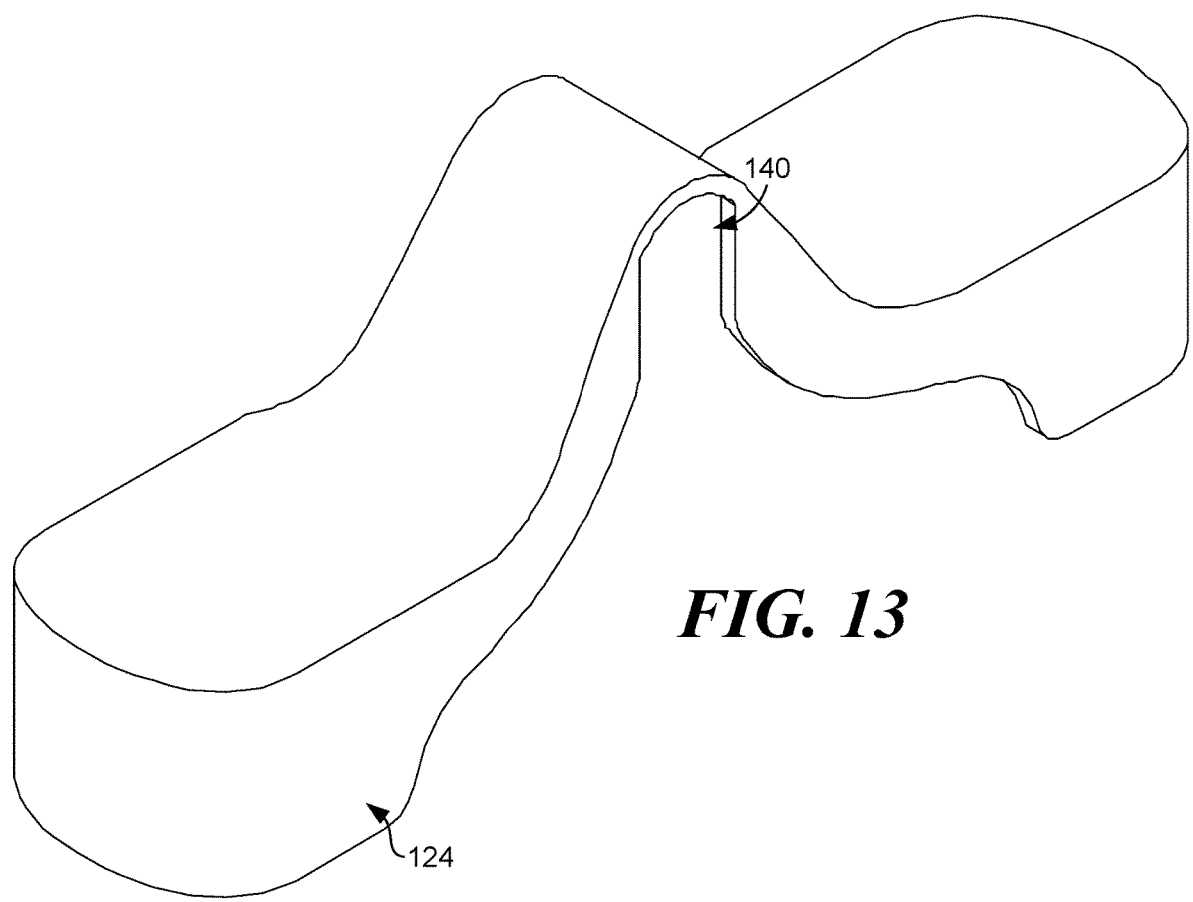
FIG. 13 is a perspective view of an enema bag cover of the enema bag system according to various embodiments of the present disclosure.
Figure 14:
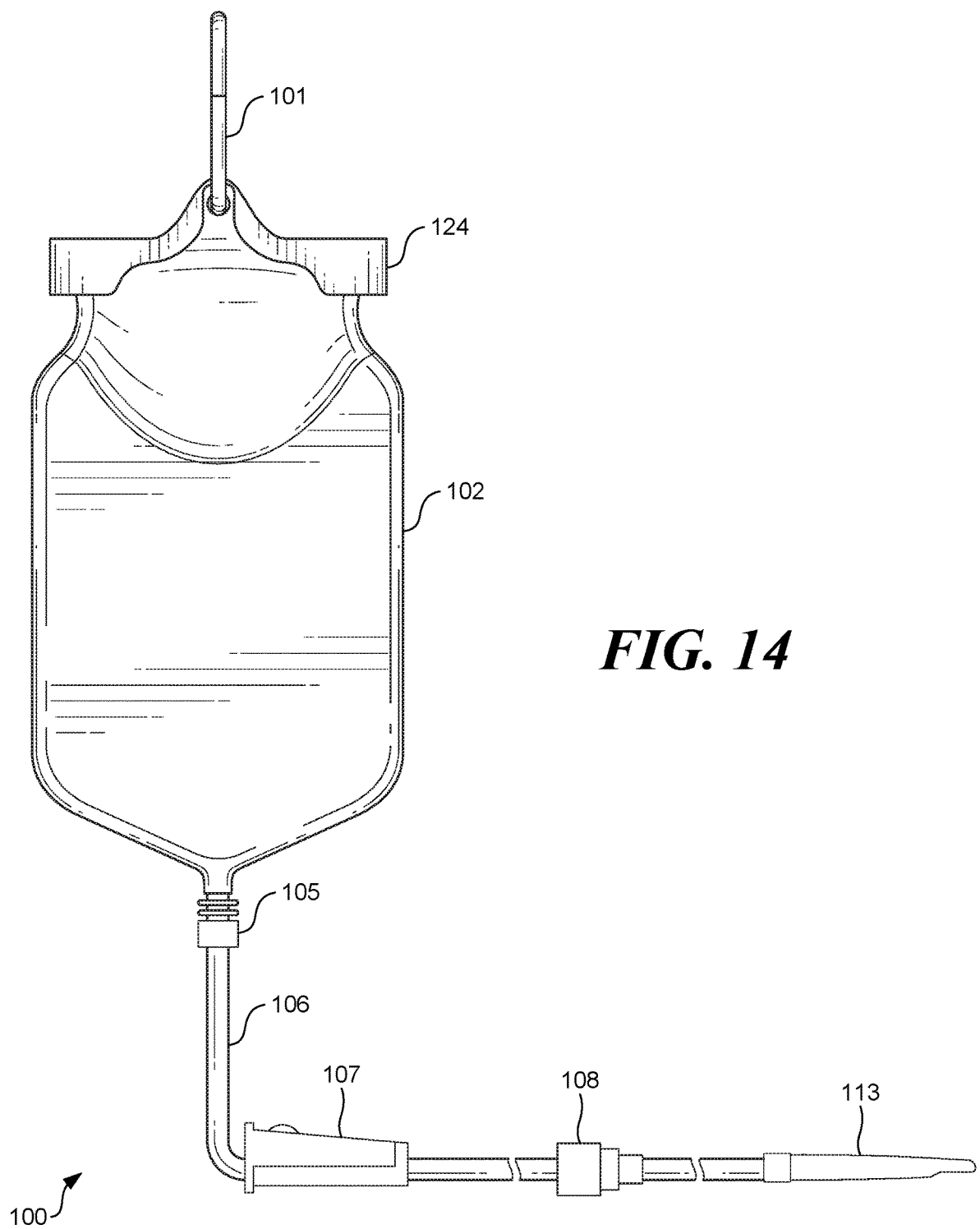
FIG. 14 is another side elevation view of the enema bag system according to various embodiments of the present disclosure.
Figure 15:
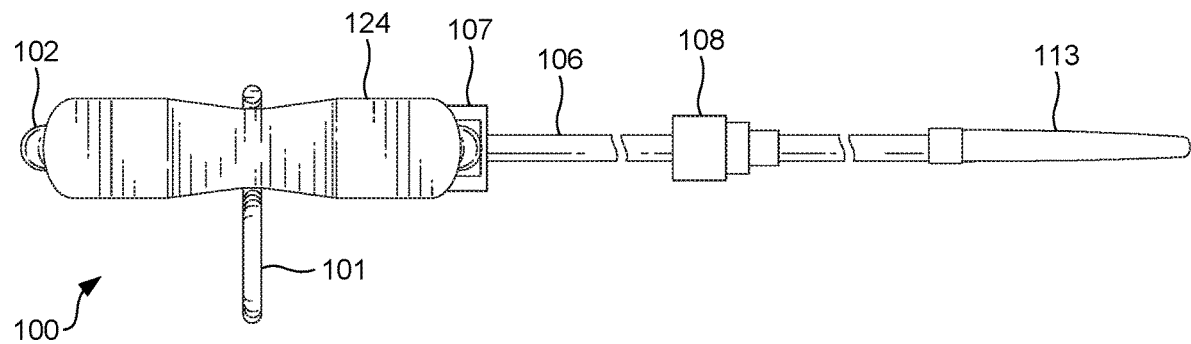
FIG. 15 is a top view of the enema bag system according to various embodiments of the present disclosure.
Figure 16:
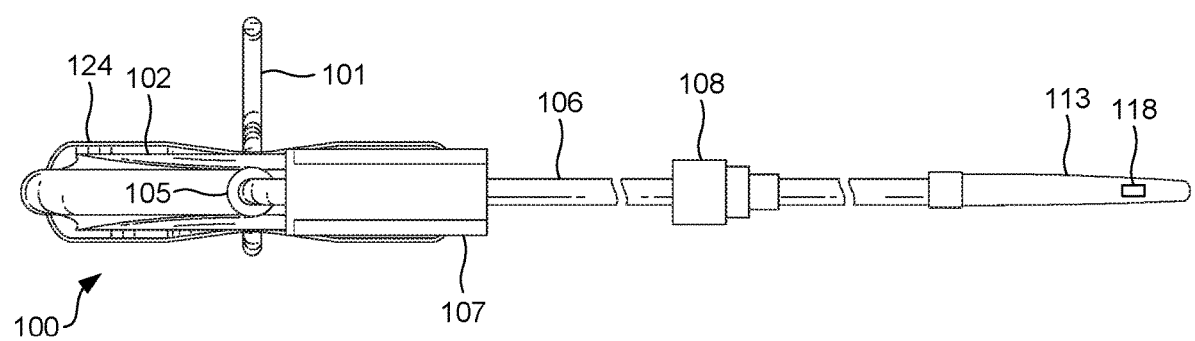
FIG. 16 is a bottom view of the enema bag system according to various embodiments of the present disclosure.

As shown in FIG. 12, an outer ring of the sealing gasket 121 can be provided with a first convex 125, second convex 126, and a third convex 127 that prevents the sealing gasket 121 from falling out of the movable nut 120. The lower part of the inner tube connector 122 is provided with an outer diameter sharp corner 123, which is processed into a unique sharp angle by a precision mold mirror impulse working, forming a tight sealing connection with the tubing 106 and tight sealing connection and vacuum, thereby ensuring that the seal does not leak water. Also, the sharp corner reversing effectively prevents the tubing 106 from falling off the inner tube connector, thereby providing a firm connection.

The features, structures, or characteristics described above may be combined in one or more embodiments in any suitable manner, and the features discussed in the various embodiments are interchangeable, if possible. In the following description, numerous specific details are provided in order to fully understand the embodiments of the present disclosure. However, the person skilled in the art will appreciate that the technical solution of the present disclosure may be practiced without one or more of the specific details, or other methods, components, materials, and the like may be employed. In other instances, well-known structures, materials, or operations are not shown or described in detail to avoid obscuring aspects of the present disclosure.

Although the relative terms such as "on," "below," "upper," and "lower" are used in the specification to describe the relative relationship of one component to another component, these terms are used in this specification for convenience only, for example, as a direction in an example shown in the drawings. It should be understood that if the device is turned upside down, the "upper" component described above will become a "lower" component. When a structure is "on" another structure, it is possible that the structure is integrally formed on another structure, or that the structure is "directly" disposed on another structure, or that the structure is "indirectly" disposed on the other structure through other structures.

In this specification, the terms such as "a," "an," "the," and "said" are used to indicate the presence of one or more elements and components. The terms "comprise," "include," "have," "contain," and their variants are used to be open ended, and are meant to include additional elements, components, etc., in addition to the listed elements, components, etc. unless otherwise specified in the appended claims. The terms "first", "second", etc. are used only as labels, rather than a limitation for a number of the objects.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. An enema bag system, comprising:
an enema bag having an enema bag opening at a top of the enema bag for filling the enema bag with solution;
an enema bag cover configured to rest on the top of the enema bag and cover the enema bag opening;
a nozzle comprising a nozzle outlet;
an anti-reflux coupler positioned between the enema bag and the nozzle through which the solution passes from the enema bag to the nozzle outlet, the anti-reflux coupler comprising:
an inlet for receiving at least a portion of the solution from the enema bag;
an outlet for expelling the solution into the nozzle; and
a check valve configured to prevent reflux of the solution from the nozzle;
tubing fluidly coupling the enema bag, the anti-reflux coupler, and the nozzle;
a pulley restrictor configured to selectively control a speed at which the solution is introduced into the nozzle and expelled from the nozzle outlet; and
an S-shape hook configured to be positioned through an aperture in the enema bag and further positioned in a recess notched in the enema bag cover, wherein a hanging of the enema bag system using the S-shaped hook creates water pressure that affects the speed at which the solution is expelled from the nozzle outlet.

2. The enema bag system of claim 1, wherein:
the pulley restrictor comprises a body, a guide, and a wheel movably coupled to the guide, the body comprising a first end and a second end;
the tubing is positioned through the body such that the wheel is positioned near the tubing;
adjustment of the wheel along the guide to the first end of the body causes pressure to be applied to the tubing and restricts flow of the solution therein; and
adjustment of the wheel along the guide to the second end of the body relieves the pressure on the tubing and permits the flow of the solution therein.

3. The enema bag system of claim 2, wherein:
the body of the pulley restrictor is triangular-shaped and comprises a recess through which the tubing is positioned;
the guide comprises a first track and a second track nested in opposing sides of the body;
the wheel comprises a first projection projecting from a first side of the wheel and a second projection projecting from a second side of the wheel; and
the first projection is received in the first track and the second projection is received in the second track.

4. The enema bag system of claim 1, wherein the check valve comprises one of: an umbrella valve; a duckbill valve; a slit-cutting valve; and a flapper valve.

5. The enema bag system of claim 1, further comprising:
a first connection at which the enema bag is removably coupled to the tubing; and
a second connection at which the tubing is coupled to other tubing and the nozzle, the second connection being provided by the anti-reflux coupler.

6. The enema bag system of claim 5, wherein at least one of the first connection and the second connection is a threaded connection or an interference fit connection.

7. An enema bag system, comprising:
an enema bag having an opening for filling the enema bag with solution and an aperture; and
an enema bag cover configured to cover the enema bag opening, the enema bag cover comprising a recess;
a nozzle comprising a nozzle outlet;
an anti-reflux coupler positioned between the enema bag and the nozzle through which the solution passes from the enema bag to the nozzle outlet, the anti-reflux coupler comprising:
an inlet for receiving at least a portion of the solution from the enema bag;
an outlet for expelling the solution into the nozzle; and
a check valve configured to prevent reflux of the solution from the nozzle;
tubing fluidly coupling the enema bag, the anti-reflux coupler, and the nozzle; and
a hook configured to be positioned through the aperture in the enema bag and configured to be positioned in the recess of the enema bag cover, wherein a hanging of the enema bag system using the hook creates water pressure that affects a speed at which the solution is expelled from the nozzle outlet.

8. The enema bag system of claim 7, wherein:
the opening of the enema bag is at a top of the enema bag for filling the enema bag with solution; and
the enema bag cover is further configured to rest on the top of the enema bag and cover the enema bag opening.

9. The enema bag system of claim 8, wherein the hook is an S-shaped hook.

10. The enema bag system of claim 7, further comprising a pulley restrictor configured to selectively control a speed at which the solution is introduced into the nozzle and expelled from the nozzle outlet.

11. The enema bag system of claim 10, wherein:
the pulley restrictor comprises a body, a guide, and a wheel movably coupled to the guide, the body comprising a first end and a second end;
the tubing is positioned through the body such that the wheel is positioned near the tubing;
adjustment of the wheel along the guide to the first end of the body causes pressure to be applied to the tubing and restricts flow of the solution therein; and
adjustment of the wheel along the guide to the second end of the body relieves the pressure on the tubing and permits the flow of the solution therein.

12. The enema bag system of claim 11, wherein:
the body of the pulley restrictor is triangular-shaped and comprises a recess through which the tubing is positioned;
the guide comprises a first track and a second track nested in opposing sides of the body;
the wheel comprises a first projection projecting from a first side of the wheel and a second projection projecting from a second side of the wheel; and
the first projection is received in the first track and the second projection is received in the second track.

13. The enema bag system of claim 7, wherein the check valve comprises one of: an umbrella valve; a duckbill valve; a slit-cutting valve; and a flapper valve.

14. The enema bag system of claim 7, further comprising:
a first connection at which the enema bag is removably coupled to the tubing; and
a second connection at which the tubing is coupled to other tubing and the nozzle, the second connection being provided by the anti-reflux coupler.

15. The enema bag system of claim 14, wherein at least one of the first connection and the second connection is a threaded connection or an interference fit connection.

16. A method, comprising:
providing an enema bag system, comprising:
an enema bag having an opening for filling the enema bag with solution and an aperture; and
an enema bag cover configured to cover the enema bag opening, the enema bag cover comprising a recess;
a nozzle comprising a nozzle outlet;
an anti-reflux coupler positioned between the enema bag and the nozzle through which the solution passes from the enema bag to the nozzle outlet, the anti-reflux coupler comprising:
an inlet for receiving at least a portion of the solution from the enema bag;
an outlet for expelling the solution into the nozzle; and
a check valve configured to prevent reflux of the solution from the nozzle;
tubing fluidly coupling the enema bag, the anti-reflux coupler, and the nozzle; and
a hook configured to be positioned through the aperture in the enema bag and configured to be positioned in the recess of the enema bag cover, wherein a hanging of the enema bag system using the hook creates water pressure that affects a speed at which the solution is expelled from the nozzle outlet.

17. The method of claim 16, wherein the enema bag system further comprises a pulley restrictor configured to selectively control a speed at which the solution is introduced into the nozzle and expelled from the nozzle outlet.

18. The method of claim 17, wherein:
the pulley restrictor comprises a body, a guide, and a wheel movably coupled to the guide, the body comprising a first end and a second end;
the tubing is positioned through the body such that the wheel is positioned near the tubing;
adjustment of the wheel along the guide to the first end of the body causes pressure to be applied to the tubing and restricts flow of the solution therein; and
adjustment of the wheel along the guide to the second end of the body relieves the pressure on the tubing and permits the flow of the solution therein.

19. The method of claim 18, wherein:
the body of the pulley restrictor is triangular-shaped and comprises a recess through which the tubing is positioned;
the guide comprises a first track and a second track nested in opposing sides of the body;
the wheel comprises a first projection projecting from a first side of the wheel and a second projection projecting from a second side of the wheel; and
the first projection is received in the first track and the second projection is received in the second track.

* * * * *